United States Patent
Dalle et al.

(10) Patent No.: US 6,964,637 B2
(45) Date of Patent: Nov. 15, 2005

(54) LARYNGOSCOPE BLADE AND HANDLE

(75) Inventors: Valéry Dalle, Gouvieux (FR); Yvan Eudes, Ezanville (FR); Eric Trellu, Lamorlaye (FR)

(73) Assignee: Vygon, Ecouen (FR)

( * ) Notice: Subject to any disclaimer, the term of this patent is extended or adjusted under 35 U.S.C. 154(b) by 0 days.

(21) Appl. No.: 10/483,211

(22) PCT Filed: Mar. 14, 2003

(86) PCT No.: PCT/FR03/00823

§ 371 (c)(1),
(2), (4) Date: Jan. 8, 2004

(87) PCT Pub. No.: WO03/077737

PCT Pub. Date: Sep. 25, 2003

(65) Prior Publication Data

US 2004/0215062 A1    Oct. 28, 2004

(30) Foreign Application Priority Data

Mar. 15, 2002 (FR) .................... 02 03226

(51) Int. Cl.⁷ .............................................. A61B 1/267
(52) U.S. Cl. ..................... 600/193; 600/185; 600/190; 600/197
(58) Field of Search ................................. 600/184, 185, 600/190–199

(56) References Cited

U.S. PATENT DOCUMENTS

| | | | | |
|---|---|---|---|---|
| 4,557,256 A | * | 12/1985 | Bauman | 600/193 |
| 4,930,495 A | * | 6/1990 | Upsher | 600/193 |
| 5,651,760 A | * | 7/1997 | Upsher | 600/193 |
| 5,702,351 A | * | 12/1997 | Bar-Or et al. | 600/190 |

* cited by examiner

Primary Examiner—Beverly M. Flanagan
(74) Attorney, Agent, or Firm—Levine & Mandelbaum

(57) ABSTRACT

The tab on the blade of a laryngoscope presents a flexible hook and an elastically-flexible wall for being inclined towards the hook when it engages a stationary abutment situated on the handle of the laryngoscope while the hook is engaged on a bar present in a cavity of the laryngoscope.

10 Claims, 2 Drawing Sheets

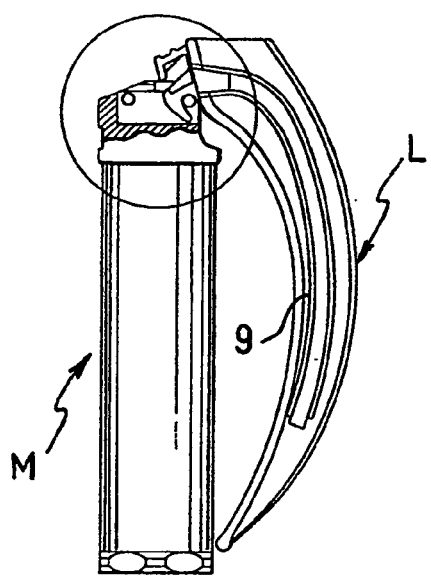
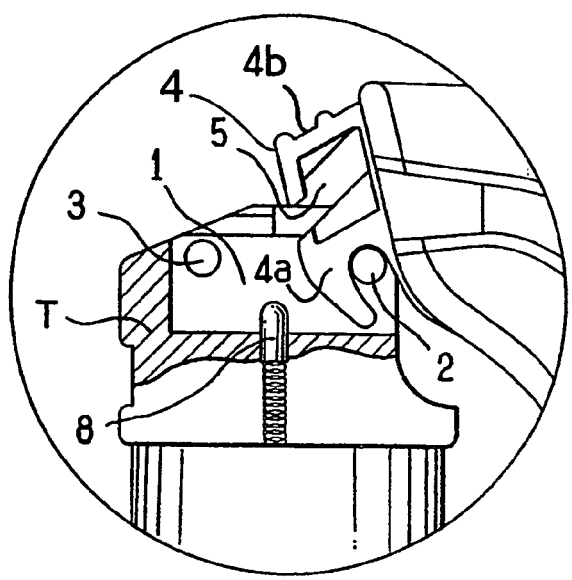
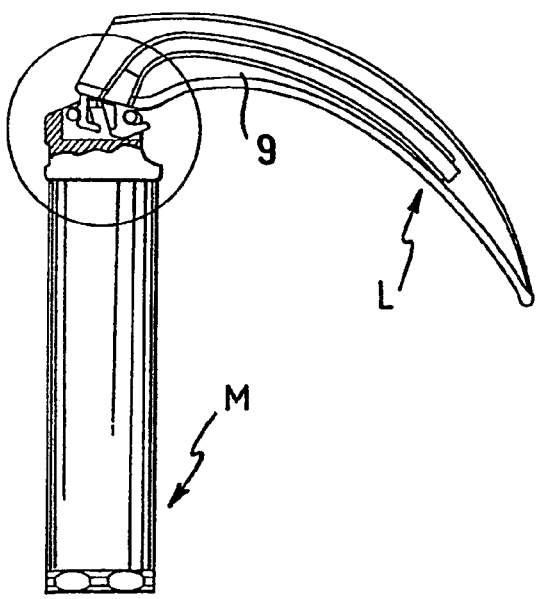
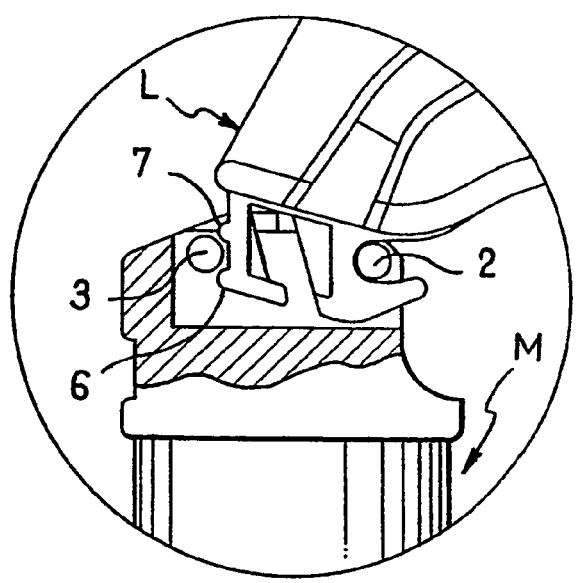

FIG_5
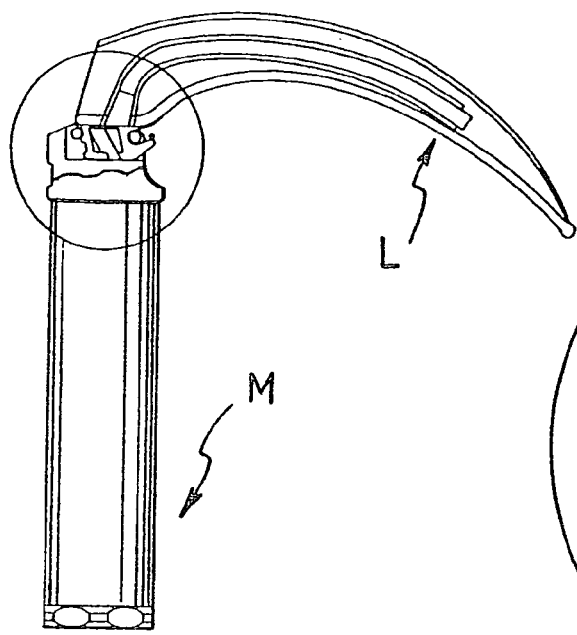
FIG_6
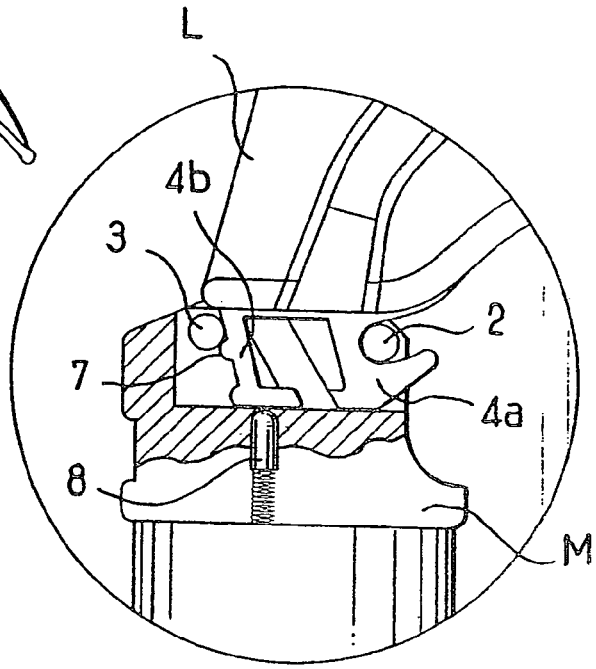
FIG_7
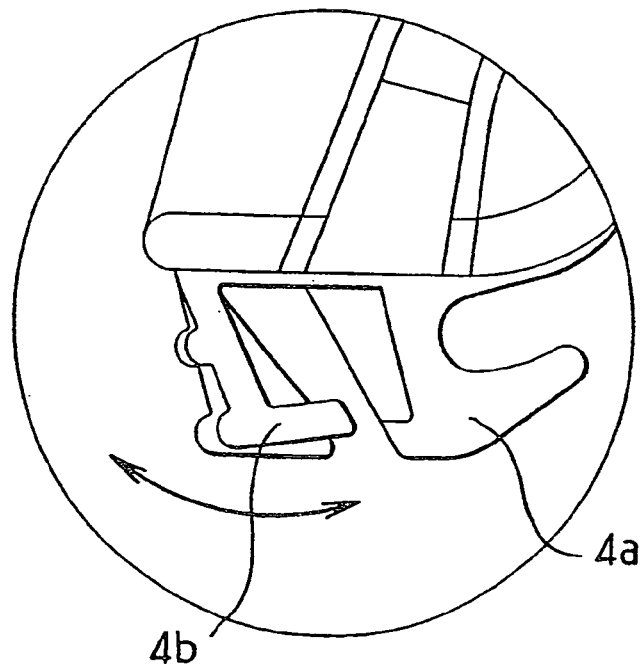

LARYNGOSCOPE BLADE AND HANDLE

BACKGROUND OF THE INVENTION

The invention relates to laryngoscopes of the type comprising a non-metallic blade for single or little-repeated use and a handle for intensive use, the blade and the handle being provided with respective means that co-operate to enable the blade to be assembled in detachable manner on the handle in at least one predefined position.

The means for assembling the blade on the handle comprise engagement means which enable the blade to be engaged on the handle, and spring effect locking means which act to hold the blade in the selected position but which can be made inactive by appropriate manipulation of the blade in order to be able to separate the blade from the handle after use.

Publication EP 0 169 497 describes an embodiment in which:

the engagement means comprise both a cavity situated in one end of the handle, which cavity is open to the outside-and contains a bar placed across the cavity, and a hook formed on a tab at one end of the blade so as to pivotally engage the bar when the tab is inserted into the cavity of the sleeve; and the locking means are constituted by a wall provided on the handle beside the cavity and receiving the tab of the blade so as to come into wedging contact with a facing wall of the tab under thrust from a spring blade fixed on the handle.

Since the handle is for repeated used, there exists a risk of fatigue in the spring blade, causing it to become less effective in locking the blade.

Publication GB 2 191 949 describes laryngoscopes having an adaptor between the blade and the handle. In one embodiment (FIGS. 4 and 5), where the means for engaging the handle on the adaptor comprise a bar and where the means for engaging the blade on the adaptor comprise a hook, the means for locking the handle on the adaptor and the means for locking the blade on the adaptor comprise respective spring-loaded balls. In another embodiment, where the means for engaging the blade on the adaptor comprise a screw passing through a tab of the blade and the adaptor, the means for locking the blade are constituted by a spring blade fixed to the tab of the blade and coming into abutment in a lateral cavity of the adaptor. Similar engagement means and locking means are provided on the handle.

SUMMARY OF THE INVENTION

An object of the present invention is to provide a laryngoscope of design that is much less expensive, and compatible for use with single-use blades.

The invention seeks to ensure that the blade is locked without compromising the cost of manufacturing the blade and without repeated use of the handle compromising the effectiveness of locking.

According to the invention, this is achieved essentially by forming an elastically flexible wall on the tab of the blade situated facing and at a distance from the hook of the tab so that the wall is constrained to incline slightly towards the hook under force when the tab is inserted in the cavity of the handle and the wall comes into contact with a stationary abutment of the handle, this inclination generating a return force seeking to cause the wall to stand up, thereby guaranteeing contact pressure between the wall and said portion of the handle.

Thus, in the invention, the spring effect can be due merely to a hole in the tab, which can be obtained by molding or by simple machining after molding.

This design thus simplifies the handle of the blade by providing the abutment for coming into contact with the flexible wall of the tab in the form of a simple stationary bar parallel to the bar which is surrounded by the hook.

Thus, the locking means on the handle comprise stationary means subject to little wear in spite of the handle being used repeatedly, and on the blade they comprise flexible means which even though they are subject to wear in the long run, they escape from this handicap since the blade is for single or little-repeated use.

DESCRIPTION OF THE DRAWINGS

There follows a description of an embodiment of a laryngoscope comprising a blade and a handle in accordance with the present invention and described with reference to the figures of the accompanying drawings, in which:

FIG. 1 is a perspective view of the blade against the handle when the hook of the blade tab has just been engaged on a bar of the handle;

FIG. 2 is a view on a larger scale showing the portion of FIG. 1 that is outlined by a circle;

FIGS. 3 and 4 are similar respectively to FIGS. 1 and 2 showing the blade after it has pivoted on said bar into a first locked position;

FIGS. 5 and 6 are similar respectively to FIG. 1 and FIG. 2, showing the blade after it has pivoted on said bar into a second locked position; and FIG. 7 is a detail view on a larger scale of the flexible wall of the blade tab.

DESCRIPTION OF THE PREFERRED EMBODIMENT

The figures show the blade L and the handle M of an embodiment of a laryngoscope in accordance with the invention.

The handle (M) is a hollow metal cylinder suitable for holding in the hand and presenting an end closed by a head T screwed onto the cylinder so as to define a cavity (1) that is open to the outside and in which there are to be found a first bar (2) and a second bar (3) which are rigid and stationary and disposed parallel to each other across the cavity.

The blade (L) is made of synthetic resin and is shaped so as to be suitable for being inserted in the mouth in order to press the tongue down against the lower jaw and to raise the epiglottis, and it presents a tab (4) at one end constituted by a hook (4a) and by a flexible ribbed wall (4b) separated from the hook by an empty gap (5). The ribbed wall presents two parallel ribs (6, 7).

The tab is dimensioned so as to be capable of being forced into the cavity in the head of the handle with the hook engaged on the bar (2) and with the flexible rib wall in contact with the other bar (3), the ribs being parallel to the bars.

Initially (FIGS. 1 and 2) the hook is engaged on the first bar and the ribbed wall remains outside the cavity in the head.

Secondly (FIGS. 3 and 4), the first rib (6) of the ribbed wall has gone past the second bar (3) and the blade is held in a first position by the second bar co-operating with the ribbed wall, the bar lying between the two ribs (6, 7) on said wall.

Thirdly (FIGS. 4 and 5), the second rib (7) of the ribbed wall has gone past the second bar (3) and the blade is locked in a second position.

In the first position and even more in the second position, the forced deflection of the flexible wall of the tab on the blade under the effect of the second bar establishes a force for holding the blade in position.

FIG. 7 is a diagrammatic view showing the deflection of the flexible wall.

The handle contains an electric battery to power a light bulb under the control of an electric contact projecting resiliently into said cavity, and the blade presents a light pipe suitable for guiding light from said bulb along the blade to a light outlet when the blade is mounted on the handle and the tab presses against said electric contact in order to switch on said light bulb.

In the figures, the electric contact is shown at (8) and the light pipe at (9). There is no need to describe these means in greater detail since they are known in themselves and do not form the subject matter of the invention.

The invention is not limited to this embodiment.

What is claimed is:

1. A non-metallic laryngoscope blade for single use, the blade comprising a tab for mounting the blade in a cavity formed at the end of a laryngoscope handle, which tab presents a portion in the form of a hook for engaging a bar extending transversely across said cavity, the blade being characterized in that the tab also presents facing the hook and at a distance therefrom, an elastically-flexible wall designed to be inclined towards the hook-shaped portion in order to lock the tab temporarily in said cavity so as to hold the blade in a defined position relative to the handle when said flexible wall is stressed so as to become inclined towards the hook-shaped portion under the effect of the wall coming into contact with a stationary abutment situated on the handle.

2. A blade according to claim 1 in which the flexible wall presents two ribs which define two positions in which the blade can be held.

3. A blade according to claim 1, made by molding a synthetic resin.

4. A laryngoscope handle for repeated use presenting a cavity at one end for receiving the tab of a laryngoscope blade and presenting in said cavity a stationary transverse bar for engaging a hook formed on the tab, the handle being characterized in that it presents a stationary abutment for coming into contact with an elastically-flexible wall formed on the tab, forcing said wall to pivot towards the hook-shaped portion so as to lock the tab in the cavity.

5. A laryngoscope handle for repeated use presenting a cavity at one end for receiving the tab of a laryngoscope blade and presenting in said cavity a stationary transverse bar for engaging a hook formed on the tab, said handle comprising a stationary abutment for coming into contact with an elastically-flexible wall formed on the tab, forcing said wall to pivot towards the hook-shaped portion so as to lock the tab in the cavity wherein said stationary abutment comprises a second bar placed transversely across the cavity.

6. A laryngoscope comprising a blade and a handle,
the blade including a tab having a portion in the form of a hook, an elastically-flexible wall, a light pipe and a light outlet,
the handle having a cavity and including a bar extending transversely across said cavity, a stationery abutment, a tube suitable for containing an electric battery for powering a light bulb, and an electric contact projecting resiliently into said cavity,
the hook portion of the tab facing said bar extending transversely across said cavity,
the elastically-flexible wall being adapted to be inclined towards the hook portion upon coming into contact with said stationary abutment in order to lock the tab temporarily in said cavity so as to hold the blade in a defined position relative to the handle,
the light pipe being adapted for guiding light from said light bulb along the blade to said light outlet when the blade is mounted on the handle and the tab of the blade pushes against said electric contact in order to switch on said light bulb.

7. A laryngoscope according to claim 6 in which the flexible wall comprises two ribs which define two positions in which the blade can be held.

8. A laryngoscope according to claim 6 wherein said stationary abutment comprises a second bar placed transversely across the cavity.

9. A laryngoscope according to claim 6 made by molding a synthetic resin.

10. A laryngoscope according to claim 8 made by molding a synthetic resin.

* * * * *